United States Patent [19]

Plewes

[11] Patent Number: 4,953,192
[45] Date of Patent: * Aug. 28, 1990

[54] SCANNING EQUALIZATION RADIOGRAPHY

[75] Inventor: Donald B. Plewes, Port Credit, Canada

[73] Assignee: The University of Rochester, Rochester, N.Y.

[*] Notice: The portion of the term of this patent subsequent to Sep. 20, 2005 has been disclaimed.

[21] Appl. No.: 408,765

[22] Filed: Sep. 18, 1989

Related U.S. Application Data

[60] Division of Ser. No. 242,644, Sep. 13, 1988, which is a continuation-in-part of Ser. No. 851,252, Apr. 14, 1986, Pat. No. 4,773,087.

[51] Int. Cl.$^5$ ............................................. G21K 5/10
[52] U.S. Cl. ..................................... 378/146; 378/145
[58] Field of Search ................. 378/62, 145, 146, 150, 378/152–153, 156–157

[56] References Cited

U.S. PATENT DOCUMENTS

| | | | |
|---|---|---|---|
| 4,670,896 | 6/1987 | Klansz | 378/156 |
| 4,675,893 | 6/1987 | Duinker et al. | 378/145 |
| 4,715,056 | 12/1987 | Vlasbloem et al. | 378/145 |
| 4,773,087 | 9/1988 | Plewes | 378/146 |
| 4,785,471 | 11/1988 | Boersma | 378/145 |
| 4,803,714 | 2/1989 | Vlasbloem | 378/62 |

OTHER PUBLICATIONS

Vlasbloem, H., et al., Amber: A Scanning Multiple-Beam Equalization System for Chest Radiography, Radiology, vol. 169 No. 1, Oct. 1988, pp. 29–34.

*Primary Examiner*—Janice A. Howell
*Assistant Examiner*—John C. Freeman
*Attorney, Agent, or Firm*—Cooper & Dunham

[57] ABSTRACT

A radiographic machine in which the exposure is equalized as between different areas of the image plane so as to enhance high spatial frequency features of the image and suppress low spatial frequency features and achieve other benefits as well. A fan beam which is wide enough to encompass the object being imaged is swept across the object and segments of that beam are individually pulse width modulated at each of a number of sampling intervals during the sweep by monostable or bistable shutter pins which either completely block or completely uncover the sectors which they control. An alternate embodiment adds beam width modulation as well, by making the shutter pins either completely block their sectors of uncover them only to the degree necessary for beam width modulation.

6 Claims, 6 Drawing Sheets

SCANNING EQUALIZATION RADIOGRAPHY

REFERENCE TO RELATED APPLICATIONS

This is a division of application Ser. No. 242,644, filed 09-13-88, which is a continuation in part of application Ser. No. 06/851,252 filed on Apr. 14, 1986, now U.S. Pat. No. 4,773,087 issued on Sept. 20, 1988. Said parent application is hereby incorporated in its entirety in this application as though fully set forth herein.

FIELD, BACKGROUND AND SUMMARY OF THE INVENTION

The invention is in the field of radiography and addresses the problem that variations in tissue thickness within the anatomy (or of object thickness in the case of inanimate bodies) can cause large variations in exposure at the image plane that can exceed the practical or desirable exposure range of the film or other imaging medium.

Various efforts have been made in the past to address this problem, in principle by seeking to reduce the range of exposure as between different areas of the image. For example, Old Delft U.S. Pat. Nos. 4,675,893, 4,677,652, 4,715,056 and 4,741,012 propose sweeping the imaged object with a fan-shaped beam of x-rays, detecting the post-patient intensity of sectors of the beam and using a feedback scheme to modulate the pre-patient intensity of sectors of the fan beam in a way which would reduce image plane variations in exposure. To this end, these patents propose the use of attenuating reeds which are moved to a greater or lesser degree into the respective sectors of the beam under servo control. The intent is to attenuate a sector to a greater or lesser degree, but it is believed that the intent is not to totally turn off a sector of radiation. A proposal which is believed similar in principle is made in Edholm U.S. Pat. No. 3,755,672, and involves using a feedback scheme to form a radiation filter which would attenuate a conical or pyramidal beam to different degrees depending on the solid angle position in the beam.

Other techniques of beam equalization are discussed in said parent patent application, including the sweeping of the sectors of a fan beam of x-rays across the object while individually controlling the respective velocities of the sectors as functions of the post-object intensities of the sectors or, in the alternative, pulsing the sectors in a pulse-width modulation scheme in which the pulse widths depend on measurements of post-object intensities of the sectors.

The techniques proposed in the Old Delft patents cited above appear to suffer from the need for precise dynamic positioning of the reeds while the fan beam sweeps the patient and for precise calibration to ensure that at any one time each reed attenuates its sector of the fan beam to the required degree, and also from the need to minimize the inherent lag between the detection of a need to attenuate to a certain degree and the movement of a reed to the precise position which could provide the needed attenuation. Similar considerations appear to apply to the Edholm patent cited above, as well the additional consideration of the need to form the filter before the imaging exposure could start. In addition, it is believed that there may be time variations in the output of the x-ray tube which may be too rapid to be accommodated by system of the type proposed in the Old Delft and Edholm patents The techniques taught in said parent application provide effective equalization for improved imaging but a need for improvement still remains. For example, the systems described in said parent application which scan a single, pencil-shaped x-ray beam in raster fashion need a significant amount of time to complete the scan or would need high x-ray output to speed up the scan. The systems which sweep the sectors of a fan beam while individually modulating the sectors through velocity modulation or pulse width modulation are described as implemented through relatively complex mechanisms for effecting the sector modulation.

Accordingly, this invention is directed to overcoming these and other limitations and to providing an imaging system in which a fan beam of penetrating radiation is swept across the object which is to be imaged while individually pulse width modulating sectors thereof as a function of post-object radiation, using a highly effective and practical feedback scheme. The object can be a patient or an inanimate object such as an industrial part. The modulation can be carried out by using bistable shutter pins. Each shutter pin has only two stable positions and transits between them rapidly under feedback control. In a blocking position a shutter pin completely blocks its sector of the fan beam and in an open position the pin completely uncovers its sector of the fan beam. The sweep of the fan beam across the object being imaged is divided into a number of sampling time intervals and each sector remains on for only a portion of each sampling interval. The duration of each such portion for each sector of the fan beam is determined by the feedback control, on the basis of detecting the post-object beam for the same sector only or for other sectors as well. The shutter pins can be moved between their blocking and open positions by pin drivers similar in construction to the pin driver heads of dot matrix printers, which in turn are controlled through a feedback loop as a function of the radiation detected at a number of angular positions in the fan beam emerging from the object. In this embodiment the shutter pins are not constrained to precise end positions. They are required to move rapidly between their end positions but the end positions need not be precisely fixed so long as in its blocking position a shutter pin substantially completely interrupts its sector of the fan beam and in its open position a shutter pin substantially completely uncovers its sector of the fan beam. The shutter pins can be in a single row across the width of the fan beam or in multiple rows. While their cross-section can have almost any shape, round pins are convenient to manufacture and use, and can be arranged in a staggered array, to overlap partly such that each beam sector controlled by a shutter pin overlaps partly with at least one adjacent sector. The feedback detector can be a linear array of detector elements extending along the width of the fan beam and moving so as to follow the sweeping motion of the fan beam, or can be a detector having a large enough detection area to receive the emerging fan beam at all times without moving or with only limited motion. In each case, the feedback detector can be in front of the image plane or behind the image plane. Of course, if it is in front of the image plane, it should be reasonably transparent to x-ray so as not to attenuate the imaging beam excessively, and its x-ray transmission characteristics should be reasonably uniform across the detection area so as not to introduce excessive mask artifacts in the image. In an alternative embodiment the modulation scheme can still be called pulse width modulation but differs in that in any one sampling time interval a shutter pin can block and uncover its sector of the fan beam two or more times. The goal still is to make the on times of the sector add u in a sampling interval to a cumulative time which is just enough for a suitable exposure level. In this case each shutter pin can be a monostable device driven by an impulse away from its stable positon against a bias force and driven back when the bias force overcomes the pin inertia. The stable position can be either when the pin is in its blocking position or in its open position. In a still alternate embodiment, beam width (or, more accurately, thickness) modulation can be added by making controlling each shutter pin such that in its open position it does not uncover its sector of the beam completely but continues to block a portion of its sector to, in efect, reduce the thickness of its sector by a controlled amount in each respective sampling time interval.

In a particular exemplary but nonlimiting embodiment of the invention, an x-ray source provides a fan beam of penetrating radiation and a scanning mechanism sweeps the fan beam across the object which is to be imaged in a sweeping direction which is transverse to the plane of the fan beam. An imager receives the fan beam which emerges from the object after suffering attenuation due to its passage therethrough and uses this emerging fan beam to form an image of the swept object. A feedback system also receives the emerging fan beam and generates a feedback signal as a function thereof, for example as a function of the radiation detected at each of a number of angular positions in the emerging fan beam. A shutter mechanism individually pulse width modulates sectors of the fan beam as a function of the feedback signal so as to reduce variations in a selected parameter of the radiation in the emerging beam received by the imager and to thereby improve a selected parameter of the image. Pulse width modulation in this context refers to dividing the sweeping motion into a number of sampling time intervals and keeping each sector on for only a part of each sampling interval, the duration of the on time in each sampling interval for each sector of the fan beam being determined as a function of the feedback signal. Alternative embodiments of the invention can combine such pulse width modulation of the sectors of a fan beam with beam width modulation of the sectors. In this context beam width modulation refers to dynamically changing the cross-sections of respective sectors of the fan beam, while the beam sweeps the object, as a function of the feedback signal. One way to do this in accordance with the invention is to change the feedback scheme such that in its open position a shutter pin need not completely uncover its sector of the fan and to precisely control the open positions of the pins so as to control the cross-section of the sectors during the on times in the sampling time intervals. In each case, the goal of the modulation scheme is to reduce variations in one or more parameters of the emerging beam received by the imager so as to improve the quality of the image formed thereby. It is desirable to establish an appropriate relationship between the dimensions of the slit collimator which defines the fan beam thickness, the speed of this collimator and the duration of a sampling time interval. Preferably, this relationship is such that the duration of a sampling time interval is an integral submultiple of the time $T_s$ that the slit collimator takes to move through the slit dimension which defines the fan beam thickness, e.g., to have 2 or 3 or 4 sampling time intervals per time $T_s$ but not a non-integral multiple such as 2.2 or 3.4 sampling time interval per $T_s$. In addition, it is desirable to synchronize the sampling time intervals with the waveform of the line voltage which powers the x-ray tube. For example, if the line voltage is at 60 Hz the number of sampling time intervals per sweep per sector of fan beam 12 can be 15, 30, 60 or 120, and the start of a time interval can be synchronized with a cycle of the line voltage waveform in a way which reduces undesirable effects of the ripple on the waveform of the power supplied to the x-ray tube. In one embodiment of the invention there can be a respective feedback detector element for each shutter pin, such that a feedback channel is made up of a shutter pin, the beam sector controlled by that pin and the feedback detector element on which that sector impinges (and the feedback network to process the detector element output and drive the pin). However, in alternate embodiments additional benefits can ensue from greater freedom in the use of the feedback detector output to control the off and on times of the beam sectors. For example, if there are shutter pins 1, 2, 3, ..., n, ..., N, where n is a positive integer, and there is a fan beam sector and a feedback detector element for each pin, the on and off time for fan beam sector n in a given sampling time interval can be determined by only the output of detector element n, or by the output of several detector elements, for example by a selected combinations of detector elements n−M through n+M, where M is an integer. For example, the on and off times of beam sector n can be controlled as a function of the combination C of the outputs of three detector elements with appropriate weigthing, i.e., by $C=[0.25(n-1)+0.5n+0.25(n+1)]$. The feedback signal for an angular position in the emerging fan beam can be derived as a function of the exposure measured at that angular position and a sector of the fan beam can therefore be turned off as soon as enough exposure has been measured at its angular position or positions in a given sampling time interval, with some accounting for feedback lag time. In the alternative, the feedback signal from each angular position for an initial part of a sampling time interval can be used to estimate how long it would take to reach a desired exposure level at each respective angular position at the feedback detector plane. The latter technique allows outputs for several angular positions at the feedback detector-plane to be combined effectively, without inaccuracies due to differences in the closure times of different shutter pins. In the alternative the latter technique can be used to reduce the effect of lag time, particularly in a case where the lag time of the feedback system is high, for example because of high transit times in the movement of pins between their end positions.

One of the advantages of the invented pulse width modulation scheme of individual sectors of a sweeping fan beam is that it can achieve highly effective and practical exposure equalization and thereby can advantageously enhance desirable qualities of the image and suppress undesirable qualities. In conceptual terms, the overall effect of exposure equalization in this context could be viewed as a way to enhance the high spatial frequencies in the image and suppress the low spatial frequencies, or as an edge enhancement In a simplistic way, this could be viewed as a result similar to that of blurring an image, for example by dividing the image into areas and replacing the pixel values in each area by the average of the pixel values in that area, and then producing a new image by subtracting on pixel-by-pixel basis the blurred image from the original image. In practical terms, the invention achieves accurate control over the relevant image qualities which is flexible enough to allow different desired levels and kinds of image qualities to be enhanced or suppressed and which adequately takes into account the practical limitations of the components and systems that are used to implement the invention. For example, the feedback in the invented system is handled in a way which remove undesirable effects of the inherent lag in feedback channels which involve mechanical motion of components such as the shutter pin. Moreover, the feedback scheme is such that it can respond rapidly enough to the inherent time variations in the output of the x-ray tube, in a way which does not detract from image fidelity. Other object and advantages of the invention will become apparent from the detailed discussion below taken in conjunction with the drawings.

DETAILED DESCRIPTION

Figure 1:
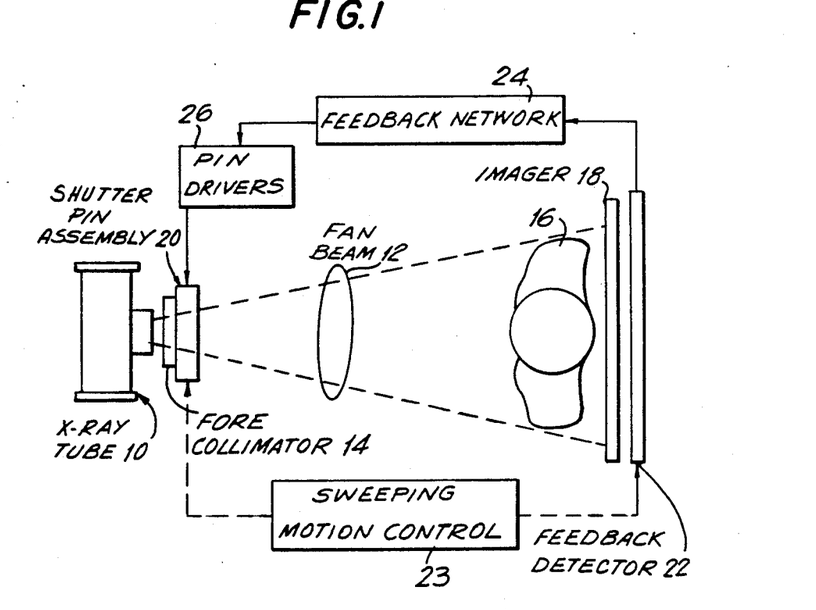
FIG. 1 is a partly top plan and partly block diagram view of exemplary components of an x-ray machine embodying an example of the invention.
Figure 2:
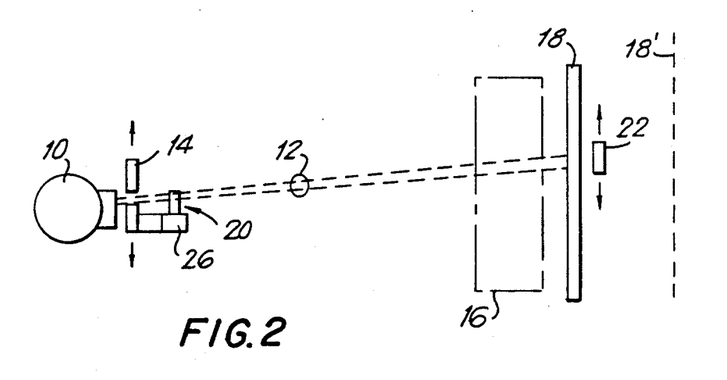
FIG. 2 is a side elevation of relevant components shown in FIG. 1.

Referring to FIGS. 1 and 2 for a general description of an embodiment of the invention, an x-ray tube 10 generates penetrating radiation which is collimated into a fan beam 12 by a fore collimator 14 and impinges on and is swept relative to a body 16, e.g., from a top to a bottom position as seen in FIG. 2. Fan beam 12 emerges from body 16 after suffering attenuation due to its passage therethrough and impinges on an imager 18 to form an image of the swept part of body 16. The beam is swept in this example by using a sweep motion control 23 to move fore collimator 14, for example along a vertical plane (as seen in FIG. 2) or along an arc centered at the source (focal) spot in x-ray tube 10. Imager 18 can be an x-ray film cassette or any other suitable imaging system such as a scintillating screen coupled to an image intensifier or any other suitable large area detector such as photostimulable phosphor layers. While it is preferred to use a large area imager which need not move while an image is being formed, it is possible to use instead an imaging detector which extends along the width of fan beam 12 and is able to receive the emerging fan beam only when aligned therewith. Such an imaging detector can be swept relative to body 16 to follow the sweeping motion of fan beam 12.

In order to achieve a desired degree and kind of image equalization, a number of sectors in impinging beam 12 are pulse width modulated by means of a shutter pin assembly 20 controlled as a function of a feedback signal which in turn is a function of the radiation detected by a feedback detector 22 at a number of angular positions in the fan beam emerging from body 16. The output of feedback detector 22, which in this example also moves under the control of sweeping motion control 23 to receive emerging beam 12 at all times, is supplied to a microprocessor 24 which in turn controls pin drivers 26 which move the shutter pins in assembly 14 between blocking and open positions. While in this example feedback detector 22 is behind the image plane, as discussed below in alternate embodiments it can be in front of the image plane, e.g., the image plane can be at position 18' illustrated in FIG. 2.

Figure 3:
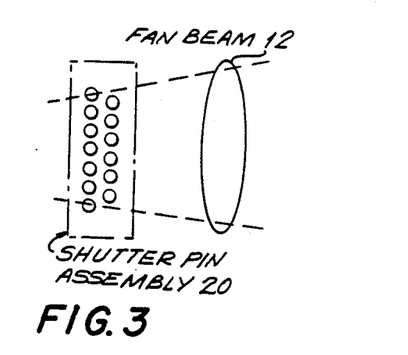
FIG. 3 is a top plan view of a shutter pin mechanism forming a part of the embodiment shown in FIG. 1.
Figure 4:
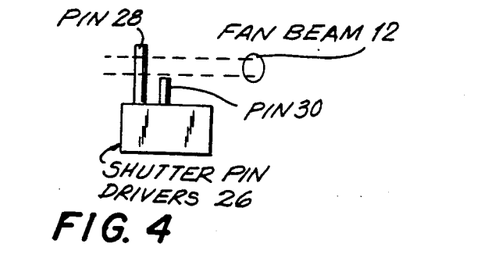
FIG. 4 is a side elevation of the mechanism shown in FIG. 3.

As seen in the enlarged view of FIGS. 3 and 4, in this example of the invention shutter pin assembly 14 has two rows of shutter pins 28 and 30. Each pin moves up and down (in the view of FIGS. 2 and 4) between a blocking position and an open position. Pin 28 is shown in its blocking position in FIG. 4 and pin 30 is shown in its open position in the same FIG. 4. When a pin 28 or 30 is in its blocking position, as is pin 28 in FIG. 4, it blocks a respective sector of fan beam 12 to prevent it from impinging on body 16. When a pin is in its open position, as is pin 30 in FIG. 4, it uncovers its respective sector of fan beam 12 to permit it to impinge on body 16. It can be said therefore that when a pin is in its blocking position, it turns off its respective sector of beam 12 and when a pin is in its open position it turns on its respective sector of beam 12.

Figure 9:
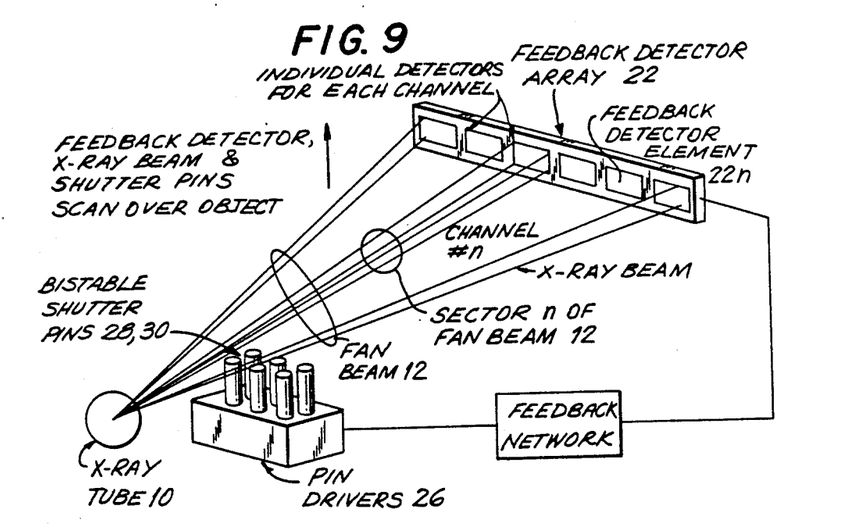
FIG. 9 is a perspective view illustrating an equalization system.

In operation, as seen in FIGS. 1, 2 and 9, as beam 12 and feedback detector 22 sweep relative to body 16, the emerging beam 12 forms an image at imager 18 and the body-attenuated radiation which emerges from detector 18 is measured at feedback detector 22 for respective angular positions in fan 12. For example, feedback detector 22 can be in the form of a row of detector elements $22_1, \ldots, 22_n, \ldots, 22_N$, where N is a positive integer, arranged next to each other along the width of fan beam 12. Each detector element can comprise, for example, a set of a scintillator crystal and a photodiode providing an electrical signal which varies as a function of the intensity of the radiation impinging thereon. In a simple case, there can be one detector element corresponding to each respective one of shutter pins 28 and 30. For example, there can be a total of 50 shutter pins numbered 1-50 and matching detector elements 1-50. Each pin turns on and off a corresponding one of sectors 1-50 of fan beam 12. Suppose that the time it takes fan beam 12 to sweep down (in the view of FIG. 2) along the part of body 16 which is to be imaged, is divided into 60 equal sampling time intervals. The feedback scheme in this case can be considered to involve 50 channels each defined by a unique shutter pin and a unique feedback detector element. During a sampling time interval a sector irradiates an area of about 1 cm² at the image plane. Consider as an example channel 25 defined by feedback detector element $22_{25}$ and shutter pin 25 which turns on and off sector 25 in fan beam 12. In the first sampling time interval $T_1$ fan beam is in its top position (as viewed in FIG. 2) and at the start of that first sampling time interval pin 25 is in its open position and therefore sector 25 of fan beam 12 is turned on. Feedback detector element $22_{25}$ measures the radiation which has travelled through body 16 along sector 25 of beam 12 and outputs a signal related to the intensity of the radiation received thereby. A feedback network 24 accumulates the output of feedback detector $22_{25}$ and, when the accumulated signal indicates that the exposure at feedback detector $22_{25}$ during this sampling time interval $T_1$ has reached a desired level, provides a control signal to pin drivers 26 to move shutter pin 25 from its open to its blocking position. Shutter pin 25 stays in its closed position for the remainder of sampling time interval $T_1$. At the start of the next sampling time interval, $T_2$, feedback network 24 supplies another control signal to pin drivers to move shutter pin 25 to its open position and starts accumulating the output of feedback detector $22_{25}$ for sampling time interval $T_2$. When the accumulated signal indicates that the exposure at feedback detector $22_{25}$ again has reached the desired level, feedback network 24 sends a control signal to pin drivers 26 to move shutter pin 25 to its blocking position where it remains for the rest of sampling time interval $T_2$. This cycle is followed for each of the remaining sampling time intervals for channel 25. The remaining channel 1-24 and 26-50 operate in the same manner.

Figure 5:
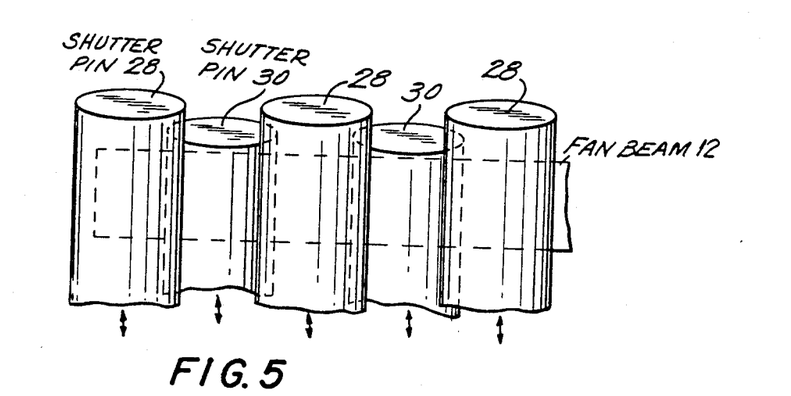
FIG. 5 is an enlarged view of overlapping shutter pins.
Figure 6:
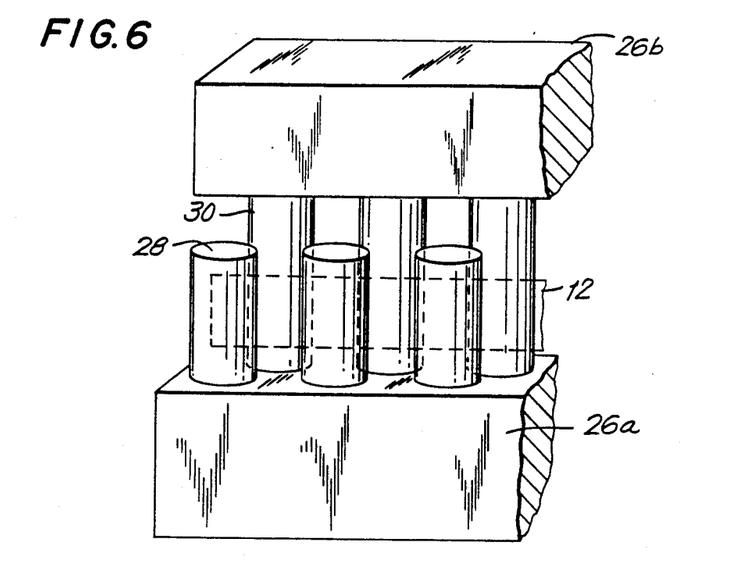
FIG. 6 is a perspective view of a part of a particular implementation of the shutter pin mechanism and FIG. 7 is a side elevation of the mechanism shown in FIG. 6.
Figure 7:
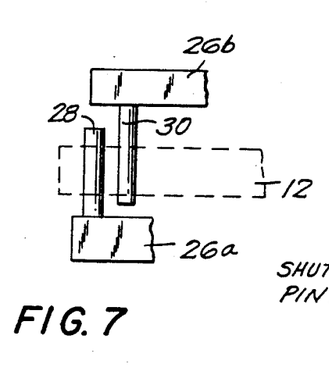

Shutter pin assembly 20 can use a single row of pins which extends across the width of fan beam 12, with the individual pins extending and moving along directions transverse to the plane of the fan beam. However, in the exemplary embodiment discussed here assembly 20 uses staggered pins, which can be considered as being in a row made up of pins 28 and a parallel row made up of pins 30, as seen in FIGS. 3-5. The pins in a row can be uniformly spaced, either linearly or angularly (with respect to the angular extent of fan beam 12), and the two rows are offset from each other such that a pin from one row controls a sector of fan beam 12 while a pin from the other row controls the adjacent sector. As seen in FIG. 5, the shutter pins overlap in part so that each sector controlled by a shutter pin overlaps in part with at least one adjacent sector. In particular, each of the two sectors at the sides of fan beam 12 overlaps in part with one adjacent sector while every other sector overlaps in part with two adjacent sectors). For example, if shutter pins 28 and 30 are the same in size and have circular cross-sections, and the interpin spacing as viewed from the source spot in tube 10 is about 85% of the pin diameter, the projected pin thickness (i.e., the thickness through which the fan beam would pass if all pins are in their blocking positions) would vary only by about 10% across the width of fan beam 12. The pin diameters can be of the order of 500-1000 microns for use in chest radiography and of the order of 100-300 microns for mammography. Suitable other diameters can be selected for modulation when imaging bodies having significantly different transmission characteristics. The pins, or at least the portions which interrupt fan beam 12, can be of any suitable material which highly attenuates x-rays, such as tantalum or tungsten, and has suitable metallurgical and mechanical characteristics. In the case of mammography, the pins can be made of steel or a similar material. In the case of chest radiography, if 50 shutter pins in a single row are used, positioned close to the source, the row length along the width of the fan beam can be about 2.5 cm. If two rows are used, with overlap as illustrated in FIGS. 3-5, the pin array length along the width of fan beam 12 can be about 2.1 cm. The transit time of a pin's motion between its blocking and open position preferably should be less than a few milliseconds and it is believed that a transit time of about 0.5 millisecond or less is the most preferred range. Fan beam 12 can be about 2-3 mm thick near the source, where the array of pins 28 and 30 is located, such that a shutter pin would have to travel along its axis only over this distance of about 2-3 mm (plus a margin of error) between its blocking and open positions. About 50-100 sampling time intervals can make up the time taken to sweep the beam across body 16. In this example, the exposure time per image is about 1 second and the dynamic range is about 40-50. Dynamic range in this context can mean the ratio between the precisely controlled maximum on time and minimum on time for a sector allowed in a particular embodiment of the system. The shutter pins can be moved between their end positions by pin drivers similar to those used in dot matrix printers. The pin drivers can be in a single row or in a double, staggered row. The pin drivers can all be on the same side of fan beam 12, as are drivers 26 in FIG. 2, or can be on opposite sides of fan beam 12, as are pin drivers 26a and 26b in FIGS. 6 and 7, where pin drivers 26a drive shutter pins 28 up to their blocking positions and down to their open positions while pin drivers 26b drive shutter pins 30 down to their blocking positions and up to their open positions.

Figure 8:
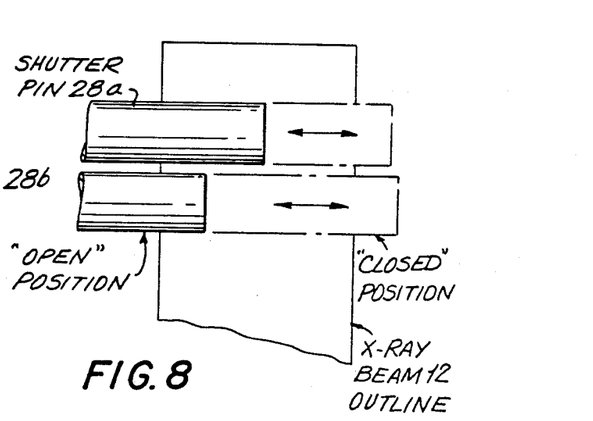
FIG. 8 is a side elevation illustrating an alternate embodiment involving both pulse width and beam width modulation.

In the embodiment discussed in detail above the shutter pins are bistable devices and their exact location at the end positions is relatively unimportant. However, if pulse width modulation of the type described above is combined with beam width modulation, the location of a shutter pin at its open position becomes important. This is illustrated in FIG. 8 for two exemplary shutter pins 28a and 28b. In its closed position each of shutter pins 28a and 28b completely block its sector of fan beam 12, as in the case of pins 28 and 30 discussed above. However, in its open position each of shutter pins 28a and 28b returns to a position in which it may block in part its sector of fan beam 12. In the illustration of FIG. 8, shutter pin 28a has returned to an open position in which it uncovers about 50% or its sector of fan beam 12 while shutter pin 28b has returned to an open position in which it uncovers about 75% of its sector of fan beam 12. In this embodiment, the degree to which each shutter pin uncovers its sector of beam 12 when brought to its open position for any one sampling time interval, is determined by a feedback signal supplied from feedback network 24 to pin drivers 24, and this feedback signal in turn is a function of the output of feedback detector 22. In this case the exact position of a shutter pin when in its blocking position is still unimportant but the exact position in the open position is important, and pin drivers 26 must be different in this respect and capable of selecting the open position. It should be clear that in this embodiment when a shutter pin is in its "open"

position, it can still block a part of its sector of fan beam 12, the degree of blocking determining how thick the sector is. Thickness in this context refers to the dimension of a sector in the direction normal to the plane of fan beam 12. It should also be clear that for any one sector the open position of the shutter pin can differ as between sampling time intervals. Note that when beam width modulation is used, and in this embodiment it can be called more precisely beam thickness modulation, it is desirable to make the thickness of the beam significantly larger than the source (focal) spot in the x-ray tube. If the focal spot were an ideal point source, then this consideration would not apply. However, in practical terms the source spot can be a round area approximately 1-2 mm in diameter. For beam width (thickness) modulation, beam 12 should be thick enough at the plane in which the shutter pins move to avoid undue penumbra effects and yet thin enough to avoid excessive transit times of the pins; a fan beam thickness of about at least about 5 mm is desirable at the plane in which the shutter pins move.

Figure 10:
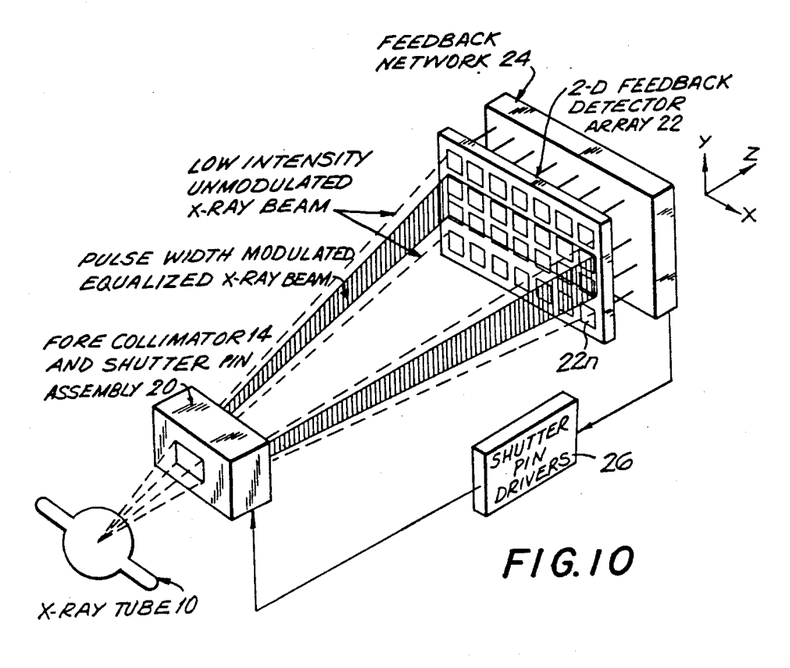
FIG. 10 is a perspective view illustrating a feedback detector which is two-dimensional in the feedback detecting plane and can be used in an alternate embodiment of the invention in which the output for two or more angular positions in a fan beam can be used to control a sector of the beam and the feedback detector can be stationary or can undergo a motion which is less that the sweeping motion of the fan beam.

Feedback detector 22 can be in the form of a linear array of detector elements $22n$, as illustrated in FIG. 9. In this simplified case only 6 detector elements are shown, but the same principle applies for the practical case of using of the order of 50-100 detector elements. Further, in this simplified case there is a one-to-one correspondence between feedback detector elements and shutter pins although, as discussed below for alternate embodiments, this is not a constraint on the invented system. In the example of FIG. 9, there are n channels for controlling n sectors of fan beam 12, and each channel has its own feedback detector element and its own shutter pin which in this example is a bistable device controlled as discussed in connection with FIGS. 1-7. Feedback detector 22 can be implemented in other ways as well. For example, feedback detector can be in a form which does not sweep the object together with fan beam 12. For this alternative, feedback detector 22 can be large enough to receive the emerging beam at all times during the sweep of beam 12 without any motion of feedback detector 22. As one example, feedback detector 22 can be a large crystal viewed by an array of photodetectors, in a structure similar to that used in nuclear cameras, or it can be large ionization chamber, for example a chamber filled with pressurized xenon with strip electrodes extending in the vertical direction (in the y-direction in FIG. 10), or it can be two-dimensional array of small detector elements, as illustrated in FIG. 10, or it can be a row of parallel long crystals, where the row extends across the width of fan beam 12 and each crystal is long enough (in the y-direction in FIG. 10) to receive the emerging beam throughout its sweep and is viewed by a photodetector attached to a vertical end. FIG. 10 illustrates a specific example of a feedback detector 22 having a rectangular array of detector elements $22_n$ arranged such that a sector of fan beam 12 impinges at any one time on at least two vertically adjacent detector elements $22_n$. While for simplicity only and array of 7×4 detector elements is shown, in practice the array is much larger, for example 50×50 or 100×100 or 100×120 elements (100 in the x-direction and 120 in the y-direction). In operation, for each sampling time interval the outputs of several detector elements are combined to control one or several shutter pins. In one example, only the outputs of the detector elements which are in the group irradiated during the time interval by the sector controlled by a respective pin are combined with each other to control that pin. The combining can be simple averaging of the outputs or it can involve a weighting function which allows the different detector elements in the group to influence the on time of the sector to different degrees. For example, the detector element or elements irradiated by the sector at the start of the sampling time interval can be allowed to exert a greater influence over the decision when to move the pin to its blocking position than elements irradiated by the same sector only later in the same sampling interval. in another example, the outputs of additional detector elements, which are not irradiated by a sector during a given sampling time interval, can contribute to the feedback signal that controls the shutter pin for that sector for that sampling interval. These additional detector elements can be spaced from the sector of interest in the x-direction or in the y-direction or both. The contributions of these additional detector elements can be weighted by any suitable one-dimensional or two-dimensional weighting function. To ensure that these contributions are not influenced by the transition of other sectors from on to off states, they can be derived only from radiation detected by the relevant detector elements during an initial portion of the relevant sampling time interval, e.g., the initial 100 μs. As another example, a combination of the outputs of a number of detector elements can be used to form a feedback signal controlling the on and off times of several shutter pins. For example, the detector elements irradiated by sectors 1-3 of fan beam 12 can be averaged and used to control the shutter pins of sectors 1-3 so that these pins move as a unit, the same can be done with sectors 4-6, etc. The effect of this is to vary the effective size of the beam sectors, with corresponding effects on the low spatial frequency rejection of the system. Stated differently, the output of a detector element can be used to control the on and off times not only of the sector which irradiates it but also of other sectors of fan beam 12. Stated still differently, the output of one detector element can contribute to controlling the on and off times of more than one sector of fan beam 12.

The properties of an image equalized in accordance with the invention are dictated primarily by the amount or exposure due to the respective sectors of fan beam 12 during the respective sampling time intervals. This amount of exposure in turn can be dictated by the on time of the sector during a sample interval and, if beam width modulation is used as well, by the cross-section of the beam during the sample interval. The one-dimensional transfer function S(f) of the system in the direction along the width of fan beam 12 can be approximated by the folloWing expression in frequency space, in which f is the image spatial frequency, Wb is the beam width at the image plane, P(f, Wd) corresponds to the Fourier transform of the profile of the radiation detected for a sector at feedback detector 20, pi is the constant 3.14, and * denotes multiplication:

$$S(f) = 1 - \text{sinc}(pi*f*Wb)*P(f, Wd) \quad (1)$$

The parameter P(f*Wd) can be controlled by weighting the relative contributions of different feedback detector elements $20n$. Stated differently, this can control the shape of the transmission measurement profile to tailor it so as to influence the transfer function in a desired manner. For example, if the outputs of a group of feedback detector elements are simply averaged over a square area which corresponds to a desired area of the image plane, the transfer function becomes:

$$S(f) = 1 - \text{sinc}(pi*F*Wb)*\text{sinc}(pi*F*Wd) \qquad (2)$$

If the weighting is not simple averaging, then the relationship expressed generally by equation (1) becomes different. As earlier noted, in the invented system the size Wb of a sector of fan beam 12 need not be the same as the area at the feedback plane which determines the parameter Wd. For example, making Wd relatively small changes the shape of the transfer function but still maintains the same bandpass. Making Wd relatively larger can increase the bandpass and simulate the effect of making larger the cross-section of the controlled sector of fan beam 12. In the example of FIG. 10, the desired combination of detector element outputs is made in feedback network 24, which can incorporate a microprocessor programmed to carry out the necessary computations and/or a look-up table in which the desired relationships can be stored. As is known in the art, the typically analog output of a detector element is digitized, in this example by suitable A/D conversion circuits in network 24, and the digital values are processed using known types of digital processing equipment to carry out the combining of signals taught by this invention.

While the shutter pins can be operated substantially independently from each other, additional benefits can be derived from permitting one channel to influence another. For example, if for a given sampling time interval $T_n$ sector n of fan beam 12 encounters very low average attenuation path while sector n+1 encounters very high attenuation due to material which partly extends into the path of sector n, if the channels operate independently it is likely that sector n+1 would overexpose the image region where it partly overlaps sector n. In accordance with the invention this can be obviated by including in feedback network 24 a circuit which allows adjacent feedback channels to influence each other, for example to ensure that the time difference between the change to blocking position of the respective shutter pins will not exceed a preset value for any two adjacent sectors of fan beam 12. Of course, this is only one example and many other interactions between and combinations of detector element outputs are within the scope of this invention.

In the alternate embodiment which uses the variant of pulse width modulation in which a pin can move in and out of its sector several times during a single sampling time interval, the overall structure and principles are the same, except that the shutter pins in assembly 20 can be monostable devices, and the modulation scheme has some characteristics of frequency modulation. In particular, each shutter pin has a single stable position and can be driven away therefrom by an impulse against a bias, for example a bias spring, in a manner very similar to driving a pin of a dot matrix printer. When the bias force overcomes the inertia due to the impulse, the shutter pins returns to its single stable position Such impulses are applied to a shutter pin driver at a frequency determined by the appropriate feedback signal, to achieve the result discussed for the earlier type of pulse width modulation. In this embodiment, the sum of the on times of a sector during a time interval should add up to a cumulative amount of on time which is sufficient for the correct level of exposure at the image plane for the relevant sector and relevant sampling time interval. The single stable position of a pin can be either its blocking position or its open position.

Significant improvements have been made through the use of scanning equalization radiography using both prepatient and post-patient collimation to reduce scatter and a feedback technique to modulate scanned x-ray beam. See, e.g.: Plewes, D. B., Computer-Assisted Exposure In Scanned Film Radiography, Proceedings International Workshop on Physics and Engineering In Medical Imaging, March 1982, pp. 79-85; Wandtke, J. C. and Plewes, D. B., Improved Chest Radiography With Equalization, RadioGraphics, Vol., 3 , No. 1 March 1983, pp. 141-154; Plewes, D. B., A. Scanning System for Chest Radiography With Regional Exposure Control: Theoretical Considerations, Med. Phys. 10(5), September/October 1983, pp. 646-654; Plewes, D. B. and Vogelstein, E., A. Scanning System For Chest Radiography With Regional Exposure Control: Practical Implementations, Med. Phys. 10(5), September/October 1983, pp. 655-663; Plewes, D. B. and Vogelstein, E., Exposure Artifacts In Raster Scanned Equalization Radiography, Med. Phys. 11(2), March/April 1984, pp. 158-165. The contents of said publications are hereby incorporated by reference in the specification as through fully set forth herein.

Figure 11:
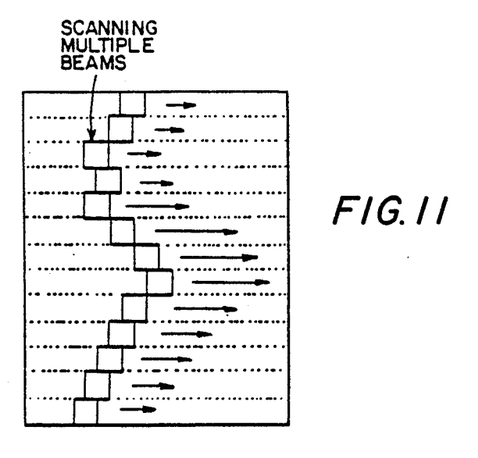
FIG. 11 illustrates scanning multiple beams.
Figure 12:
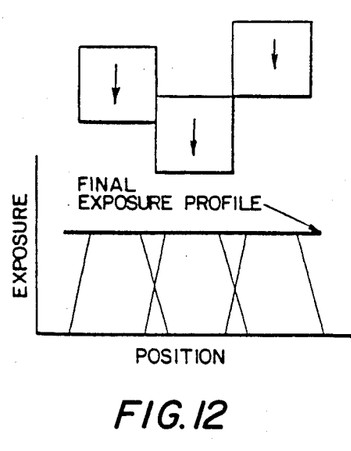
FIG. 12 illustrates exposure overlap by three scanning x-ray beams moving at the same velocity.
Figure 13:
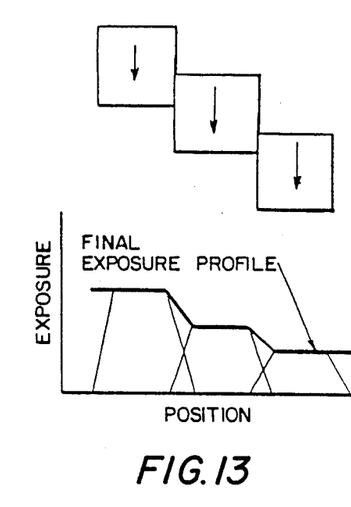
FIG. 13 illustrates exposure overlap by three scanning x-ray beams moving at different velocities along respective scan lines.

In order to reduce exposure time, a fan beam divided into a number of segments can be used, each segment in effect scanning its own scan line, and with a number of scan lines scanned simultaneously. This is illustrated in FIG. 11, where a number of segments, each represented by a respective square, scan along respective horizontal scan lines indicated by respective arrows. If velocity modulation is used, then each segment can be considered an individual scanning beam and can be individually velocity modulated, in the manner discussed for velocity modulation of single beam systems in said publications. If the pre-patient collimators producing the individually scanned segments of the fan beam are placed close to the x-ray focal spot, then their exposure profiles on the film or image intensifier will be blurred or overlapped, as illustrated in FIG. 12. If the segments are moving at the same speed across the patient, and the adjacent apertures for the segments are such that their edges are collinear, then the blur of adjacent scan lines will combine to produce a substantially uniform exposure, as illustrated in FIG. 12. However, if the beam are moving at different scan line velocities, then the receptor exposure from each scan line will differ, and the transition between adjacent scan lines will be rendered as a smooth gradation, as illustrated in FIG. 13. A conventional scatter rejection grid can be used in place of a rotating post-patient collimator in the system discussed in connection with FIGS. 11-13. If a fan beam is divided into three segments, in an exemplary test system, three pre-patient scanning apertures can be used, moved by small linear stepper motors. Each stepper motor is controlled for velocity modulation of the respective segment in the manner discussed for single beam systems in said prior publications authored or co-authored by Dr. Plewes.

Figure 14:
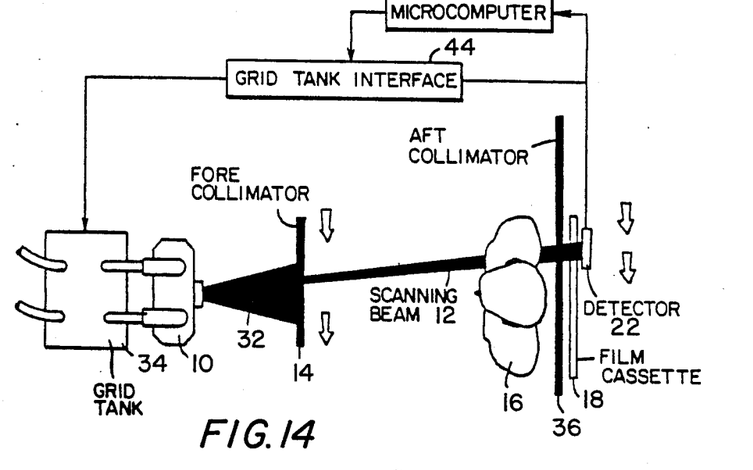
FIG. 14 is a schematic diagram of a scanning x-ray system to which certain aspects of the invention can be applied.
Figure 15:
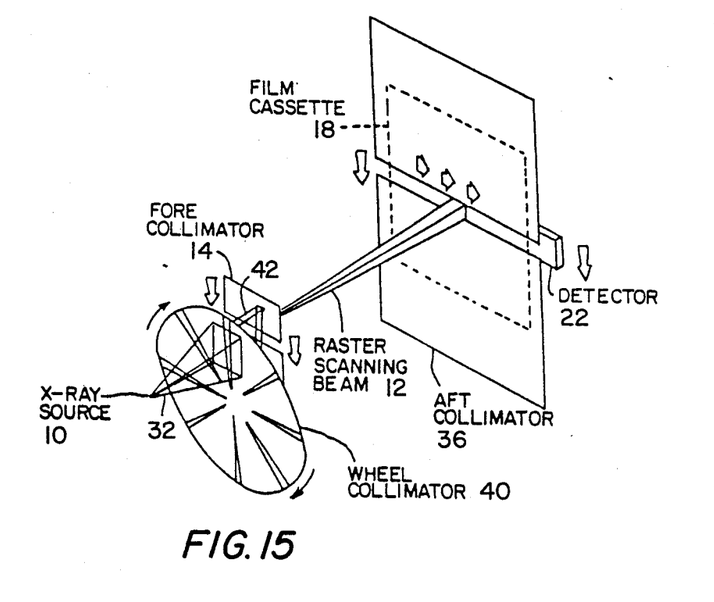
FIG. 15 is a perspective view of certain components of the scanning x-ray system of FIG. 14.

Referring to the schematic diagram of FIG. 14 an x-ray beam 32 comes from a source which comprises an x-ray tube 10 powered by a grid tank 34. Beam 32 is initially cone-shaped or pyramid-shaped, but is collimated to a scanning beam 12 by a pre-patient collimator (fore collimator) 14 to scan a patient 16 in raster fashion. A post-patient collimator (aft collimator) sweeps the patient in synchrony with the pre-patient collimator such that scanning beam 12 scans a film cassette 18 (or some other receptor) in a raster of overlapping scan lines. A post-patient detector 22 receives radiation which has passed through receptor 18, and its output is used by microcomputer 44 to control grid tank 34 through interface 44 such that scanning beam 12 is modulated in a desired manner to achieve a desired result, for example in terms of image quality, SN ratio and/or patient dosage. Referring to the partial view of FIG. 15, a rotating wheel collimator 40 is between x-ray source 10 and pre-patient (fore) collimator 18 to collimate the cone- (or pyramid-) shaped x-ray beam 10 from source 10 into a fan 42, which in turn is collimated by the linear slit of collimator 14 into raster scanning beam 12 which can be, as a nonlimiting example, of a rectangular section of about 3.5×3.5 cm at the plane of receptor 18. Post-receptor detector 22, used in the feedback loop, can move with scanning beam 12, both along the raster lines and from raster line to raster line (as in FIG. 14), or it can be as long as a raster line so that it only need move from raster line to raster line with scanning beam 12 (as in FIG. 15). In the type of an x-ray system illustrated in FIGS. 14 and 15, scanning beam 12 can be modulated by dynamically varying its velocity along a scan line (velocity modulation) or by pulsing it at a selected frequency and at selected pulse widths (pulse width modulation or PWM) or by dynamically modulating its intensity and/or hardness or by dynamically modulating its shape (e.g., cross-section) or by a combination of sub-combination of the foregoing types of modulation. Some of those types of modulation are discussed in greater details in the publications authored or co-authored by Dr. Plewes, cited earlier and incorporated by reference.

I claim:

1. A system for imaging an object with scanning sectors of penetrating radiation which are modulated prior to impinging on the object to control the local exposure time at an imaging receptor without substantially varying the intensity of the radiation contributed to sectors exiting the modulation by respective points at the origin of the radiation, comprising:

a source which generates penetrating radiation at an origin;

a scanner-modulator which receives penetrating radiation from said origin and concurrently modulates a plurality of sectors thereof to form respective modulated sectors exiting the scanner-modulator without substantially varying the intensity of the radiation contributed to the sectors exiting the scanner-modulator by respective points at said origin, and scans said object with said exiting sectors to cause respective object-attenuated sectors to emerge from the object; and an imaging receptor which receives said object-attenuated sectors and forms an image of said object;

said scanner-modulator comprising moving modulating elements which mechanically, simultaneously and individually modulate said sectors to control the local exposure time at said imaging receptor; and wherein said sectors of radiation are arrayed in a direction transverse to the direction of said scanning.

2. A system as in claim 1 in which said scanner-modulator scans said exiting sectors relative to said object at respective different velocities to carry out velocity modulation.

3. A system as in claim 1 in which said source is an x-ray tube, said origin is a focal spot within said tube, said penetrating radiation is x-rays, and said imaging receptor is an x-ray film.

4. A method of imaging an object with penetrating radiation in which sectors of said radiation are modulated to control the local exposure time for forming an image of the object without substantially varying the intensity of the radiation contributed to the sectors exiting the modulation by respective points at the origin of the radiation, comprising the steps of:

generating penetrating radiation at an origin;

modulating sectors of said radiation to form modulated sectors without substantially varying the intensity of the radiation contributed to the sectors exiting the modulation by respective points at said origin while scanning the object with said exiting sectors to cause respective object-attenuated sectors to exit the object; and using said object-attenuated sectors to form an image of the object;

said modulating and scanning step comprising mechanically, individually and simultaneously modulating said sectors with moving modulating elements to control the local exposure time of the radiation used to form said image of the object; and said scanning being in a scanning direction which is transverse to a direction along which said sectors are arrayed.

5. A method as in claim 4 in which said modulating and scanning step comprises scanning said exiting sectors relative to said object at different velocities to carry out velocity modulation.

6. A method as in claim 4 in which said penetrating radiation is x-rays, said origin is a focal spot in an x-ray tube and said imaging receptor comprises an x-ray film.

* * * * *